US00PP23753P3

(12) United States Plant Patent
Verboom

(10) Patent No.: US PP23,753 P3
(45) Date of Patent: Jul. 16, 2013

(54) ***HELLEBORUS* PLANT NAMED 'VERBEAUTY2'**

(50) Latin Name: *Helleborus niger*
Varietal Denomination: VERBEAUTY2

(76) Inventor: Johannes Verboom, Zevenhuizen (NL)

( * ) Notice: Subject to any disclaimer, the term of this patent is extended or adjusted under 35 U.S.C. 154(b) by 405 days.

(21) Appl. No.: 12/927,329

(22) Filed: Nov. 12, 2010

(65) Prior Publication Data

US 2012/0124708 P1 May 17, 2012

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Kent L Bell
(74) *Attorney, Agent, or Firm* — Cassandra Bright

(57) ABSTRACT

A new and distinct *Helleborus niger* cultivar named 'VERBEAUTY2' is disclosed, characterized by distinctive pure white flowers on a strong, compact plant. Plants of the new variety produce an abundance of flowers and are tolerant of high light conditions. The new variety is a *Helleborus*, normally produced as an ornamental plant.

1 Drawing Sheet

Latin name of the genus and species: *Helleborus niger.*
Variety denomination: 'VERBEAUTY2'.

BACKGROUND OF THE INVENTION

The new cultivar was discovered as a chance, mutation by the inventor, Johannes Teúnis Verboom, a citizen of the Netherlands. The parent is the unpatented variety *Helleborus niger* 'Verboom Beauty'. The new variety was discovered in 2006, by the inventor in a commercial greenhouse in Zevenhuizen, the Netherlands. The seedling was discovered as a whole plant mutation of the parent variety.

Asexual reproduction of the new cultivar 'VERBEAUTY2' by tissue culture was first performed in 2006, at a commercial laboratory in the Netherlands. Multiple generations have since been produced and have shown that the unique features of this cultivar are stable and reproduced true to type on successive generations.

SUMMARY OF THE INVENTION

The cultivar 'VERBEAUTY2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VERBEAUTY2' These characteristics in combination distinguish 'VERBEAUTY2' as a new and distinct *Helleborus* cultivar:

1. Distinctive pure white flowers
2. Abundant flowering.
3. Tolerance for high light conditions.
4. Strong, very compact, short plants.

PARENT COMPARISON

Plants of the new cultivar 'VERBEAUTY2' are similar to plants of the parent, *Helleborus niger* 'Verboom Beauty' in most horticultural characteristics, however, plants of the new cultivar 'VERBEAUTY2' produce more flowers per plant, grow faster and are more tolerant of high light conditions than 'Verboom Beauty' Additionally the new variety has more green coloration on the peduncles than 'Verboom Beauty'.

COMMERCIAL COMPARISON

'VERBEAUTY2' can be compared to the commercial variety *Hellborus niger* 'HGC Jacob'; U.S. Plant Pat. No. 17,799. Plants of the two varieties are similar in most horticultural characteristics, however, plants of 'VERBEAUTY2' are stronger, and produce most flowers. Additionally plants of the new variety are shorter and spread wider than 'HGC Jacob'.

The new variety can also be compared to *Helleborus niger* 'COSEH230' U.S. Plant Pat. No. 21,242. *Helleborus niger* 'Verbeauty2' and 'COSEH230' are similar in most horticultural characteristics, however 'VERBEAUTY2' has a better tolerance for high light conditions, and typically has more flowers and flower buds per plant.

BRIEF DESCRIPTION OF THE PHOTOGRAPH

The accompanying photograph illustrates in full color a typical plant of 'VERBEAUTY2' grown in a greenhouse, in Zevenhuizen, the Netherlands, in a commercial 17 cm container. Age of the plant photographed is approximately 30 months from a stage three tissue culture explant. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'VERBEAUTY2' plants grown during the winter months in a greenhouse in Evergem, Belgium. The growing temperature ranged from 1° C. to 30° C. daytime and 1° to 20° C. at night. Measurements and numerical values represent averages of typical plant types. No growth regulators or other chemical treatments were given.

Botanical classification: *Helleborus niger* 'VERBEAUTY2'.

Propagation:

Time to initiate roots: About 14 to 21 days at approximately 11° C. or lower.

Root description: Fleshy, irregular diameter roots.

Propagation method: Tissue culture.

PLANT

Growth habit: Flattened globular; leaves and individual flowers grow directly from the base.

Pot size of plant described: 17 cm.

Height: Approximately 18.6 cm.

Plant spread: Approximately 32.7 cm.

Growth rate: Moderate.

Branching characteristics: No main or lateral branches present, leaves and individual flowers grow directly from the base.

FOLIAGE

Leaf:

*Arrangement*.—Alternate, growing directly from the base.

*Leaflets*.—Shape: Obovate. Quantity: Approximately 4 per stem. Average Length: 5.6 cm. Average Width: 2.7 cm.

*Individual leaf blades*.—Shape of blade: Pedate, with an average of 7 leaflets. Apex: Acute. Base: Cuneate. Margin: Serrate. Texture of top surface: Smooth, moderately glossy. Texture of bottom surface: Smooth, moderately glossy. Pubescence: No leaf pubescence. Aspect: Upright to slightly outward.

*Color*.—Young foliage upper side: Near RHS Green N137A. Young foliage under side: Near RHS Yellow-Green 147B. Mature foliage upper side: Near RHS Green N137A. Mature foliage under side: Near RHS Grey-Green 189A.

*Venation*.—Type: whole leaf: laciniate; leaflet: pinnate. Venation color upper side: Near RHS Green 143B. Venation color under side: Near RHS Yellow-Green 147B.

*Petiole*.—Length: Approximately 11.1 cm. Diameter: Approximately 0.4 cm. Color: Near RHS Yellow-Green 146C , heavily dotted Yellow-Green 152A and Greyed-Green 197A and 197B. Texture: Smooth, dull.

*Stipule*.—Length: Approximately 3.1 cm. Diameter: Approximately 2.8 cm. Color: Near RHS Green 143C. Texture: Smooth, dull, crinkled.

FLOWER

Natural flowering season: Winter (December to February).

Days to flowering from rooted plantlet: 2 to 2 and a half years.

Inflorescence and flower type and habit: Individual flowers grow directly from the base, flowers single.

Rate of flower opening: 5 to 10 days from bud to fully opened flower.

Flower longevity on plant: Approximately 12 days.

Persistent or self-cleaning: Self-cleaning.

Bud:

*Shape*.—Ovate, flattened.

*Length*.—Approximately 1.9 cm.

*Diameter*.—1.1 cm at narrowest; 1.3 cm at widest.

*Color*.—Near RHS White NN155 D, base more greenish; Green-White 157D.

Flower size:

*Diameter*.—6.3 cm.

*Depth*.—1.8 cm.

*Aspect*.—Upright to slightly outward.

Sepals:

*Quantity*.—5.

*Arrangement*.—Rotate.

*Length*.—3.4 cm.

*Width*.—3.3 cm.

*Shape*.—Broad obovate to orbicular.

*Apex*.—Rounded.

*Base*.—Cuneate.

*Margin*.—Entire.

*Texture, upper and lower surfaces*.—Smooth.

*Appearance*.—Very slightly glossy.

*Color*.—When opening, upper surface: Near RHS White NN155D, base Yellow-Green 145C. When opening, lower surface: Near RHS White NN155D, base Yellow-Green 145C. Fully opened, upper surface: Near RHS White NN155D, base Yellow-Green 145C. Tip Green-White 157C. Fully opened, lower surface: Near RHS White NN155D, base Yellow-Green 145C. Tip Green-White 157C.

Bracts:

*Quantity per flower*.—1.

*Length*.—2.5 cm.

*Diameter*.—1.8 cm.

*Attachment*.—Decurrent, placed approximately 3.5 cm below flower.

*Aspect*.—Slightly upright, in an average angle of 30° (0°=vertical).

*Color*.—Towards base: Near RHS Yellow-Green 144B. Apex: Near RHS Yellow-Green 144B.

Pedicels:

*Length*.—14.8 cm.

*Diameter*.—0.3 cm.

*Angle*.—About 75° to the soil (=0°) .

*Strength*.—Very strong.

*Texture*.—Smooth, slightly glossy.

*Color*.—Near RHS Yellow-Green 145A, heavily dotted Greyed-Purple 183B.

Fragrance: No fragrance.

REPRODUCTIVE ORGANS

Stamens:

*Number*.—Approximately 80.

Anthers:

*Shape*.—Basifixed, kidney-shaped.

*Length*.—Approximately 1.0 cm.

*Color*.—filament Near RHS NN155D, anther RHS Yellow 4A.

*Pollen*.—Color: Near RHS Yellow 7B. Quantity: moderate.

Pistil:

*Number*.—Average: 8.

*Length*.—0.7 cm.

*Style*.—Length: 0.65 cm. Color: Near RHS Yellow-Green 145D.

*Stigma*.—Shape: club-shaped. Color: RHS 145D to 157C. Ovary Color: RHS 145D.

OTHER CHARACTERISTICS

Other flower characteristics: An average of 14 flattened nectaries placed at the base of the filaments, average length: 7 mm, average width at the top: 2 mm, average width at the base: 0.5 mm, near RHS Yellow-Green 151D, base near RHS Green-White 157D.

Seeds and fruits: Not observed to date.

Disease/pest resistance: Neither resistance nor susceptibility to pathogens and pests common to *Helleborus niger* have been observed.

Temperature tolerance: The new variety tolerates temperatures to USDA Zone 3.

What is claimed is:

1. A new and distinct cultivar of *Helleborus* plant named 'VERBEAUTY2' as herein illustrated and described.

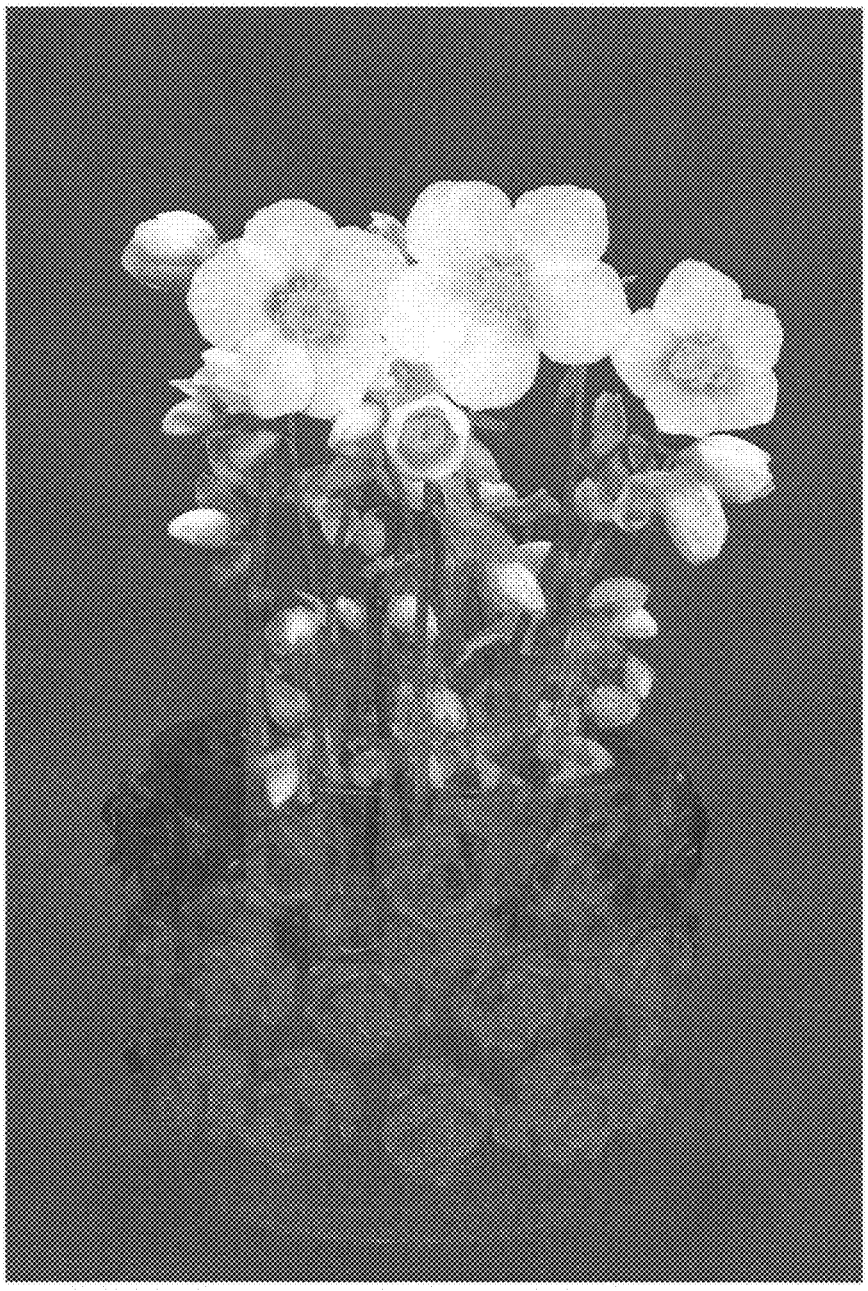

* * * * *